US00PP09026P

United States Patent [19]

VandenBerg

[11] Patent Number: Plant 9,026

[45] Date of Patent: Jan. 3, 1995

[54] CHRYSANTHEMUM PLANT NAMED KIMBERLY

[75] Inventor: Cornelis P. VandenBerg, Salinas, Calif.

[73] Assignee: Yoder Brothers, Inc., Barberton, Ohio

[21] Appl. No.: 169,189

[22] Filed: Dec. 20, 1993

[51] Int. Cl.[6] ..... A01H 5/00

[52] U.S. Cl. ..... Plt./82.4

[58] Field of Search ..... Plt. 74.1, 82.4

REFERENCES CITED

U.S. PATENT DOCUMENTS

PLT 4120 10/1977 Shoesmith .....PLT/82.4

*Primary Examiner*—Howard J. Locker

*Attorney, Agent, or Firm*—Foley & Lardner

A Chrysanthemum plant named Kimberly particularly characterized by its flat capitulum form; daisy capitulum type; light purple ray floret color; diameter across face of capitulum of 47 to 52 mm when fully opened; branching pattern is spreading and prolific, with 9 breaks after pinch when grown outside under natural daylength in fall flowerings and 5 to 8 breaks when grown in 10 cm pots for spring flowerings; natural season flower date of September 2 to 7 when planting rooted cuttings on June 21 to 25 in Salinas, Calif., and October 5 to 17 when planting rooted cuttings June 11 to June 18 in Hightstown, N.J.; flowering response of 46 to 53 days after rooting in no light/no shade programs in spring in Salinas; plant height of 30 to 36 cm when grown in fall under natural daylength with no growth regulators in New Jersey, and 18 to 23 cm when grown in 10 cm pots in spring with no growth regulator applications; and durable, uniform performance.

The present invention comprises a new and distinct cultivar of Chrysanthemum, botanically known as *Dendranthema grandiflora*, and referred to by the cultivar name Kimberly.

Kimberly, identified as 8078 (89-707002), was originated from an open pollination program, where the best breeding lines were selected by Cornelis P. VandenBerg, flowered under controlled conditions outdoors and left to be pollinated by bees, in Salinas, Calif. in September 1988.

The female parent of Kimberly was the cultivar identified as Megan, disclosed in U.S. Plant Pat. No. 8,756, and described as a garden mum with a red-purple ray floret color and a decorative capitulum type with many disc florets in the fall to a daisy with many ray florets in spring flowerings.

The male parent of Kimberly is unknown, since the female parent of Kimberly was open pollinated.

Kimberly was discovered and selected as one flowering plant within the progeny of the stated cross by Cornelis P. VandenBerg in September 1989, in a controlled environment in Salinas, Calif.

The first act of asexual reproduction of Kimberly was accomplished when vegetative cuttings were taken from the initial selection in November 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Kimberly are firmly fixed and are retained through successive generations of asexual reproduction.

Kimberly has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Kimberly, which, in combination, distinguish this Chrysanthemum as a new and distinct cultivar:

1. Flat capitulum form.
2. Daisy capitulum type.
3. Light purple ray floret color.
4. Diameter across face of capitulum of 47 to 52 mm when fully opened.
5. Branching pattern is spreading and prolific, with 9 breaks after pinch when grown outside under natural daylength in fall flowerings, and 5 to 8 breaks when grown in 10 cm pots for spring flowerings.
6. Natural season flower date of September 2 to 7 when planting rooted cuttings on June 21 to 25 in Salinas, Calif., and October 5 to 17 when planting rooted cuttings June 11 to June 18 in Hightstown, N.J.
7. Flowering response of 46 to 53 days after rooting in no light/no shade programs in spring in Salinas.
8. Plant height of 30 to 36 cm when grown in fall under natural daylength with no growth regulators in New Jersey, and 18 to 23 cm when grown in 10 cm pots in spring with no growth regulator applications.
9. Durable, uniform performance.

The accompanying photographic drawings show typical inflorescence and leaf characteristics of Kimberly, with the colors being as nearly true as possible with illustrations of this type.

Sheet 1 is a color photograph of Kimberly grown as a pinched garden mum under natural season outside conditions in Salinas, Calif. Plants were grown outside and dug and transplanted into 15 cm bulb pans at flowering time for photography purposes.

Sheet 2 is a black and white photograph of three views of the inflorescence of Kimberly.

Sheet 3 is a black and white photograph showing the upper and under sides of the leaves of Kimberly at 3 stages of development (mature, intermediate and immature). In sheets 2 and 3 a measuring tape in centimeters has been added.

Of the commercial cultivars known to the inventor, the most similar in comparison to Kimberly is the cultivar identified as Adorn, disclosed in U.S. Plant Pat. No. 6,059. Reference is made to attached Chart A, which compares certain characteristics of Kimberly to the same characteristics of Adorn. Similar traits are capitulum form and type, and controlled flowering response in spring and plant height. Kimberly differs from Adorn in that Kimberly has a lighter purple flower color (75B to 75C compared to the darker purple 78B-C color of Adorn), a substantially smaller flower with better flower form, a more spreading branching pattern, and a slower natural season flower date than Adorn.

In the following description, color references are made to The Royal Horticultural Society Colour Chart. The color values were determined on plant material grown as a pinched garden mum grown outdoors in Salinas, Calif. on Sep. 2, 1993.

Classification:

*Botanical.*—*Dendranthema grandiflora* cv Kimberly.

*Commercial.*—Flat daisy spray pot mum and garden mum.

INFLORESCENCE

A. Capitulum:

*Form.*—Flat.

*Type.*—Daisy.

*Diameter across face.*—47 to 52 mm when fully opened.

B. Corolla of ray florets:

*Color (general tonality from a distance of three meters).*—Light purple.

*Color (upper surface).*—75B to 75C.

*Color (under surface).*—75B to 75D.

*Shape.*—See photograph.

C. Corolla of disc florets:

*Color (mature).*—17C.

*Color (immature).*—14A tinged with 144C.

D. Reproductive organs:

*Androecium.*—Present on disc florets only; moderate pollen.

*Gynoecium.*—Present on both ray and disc florets.

PLANT

A. General appearance:

*Height.*—Plant height of 30 to 36 cm when grown in fall under natural daylength with no growth regulators in New Jersey, and 18 to 23 cm when grown in 10 cm pots in spring with no growth regulator applications.

*Branching pattern.*—Spreading and prolific, with 9 breaks after pinch when grown outside under natural daylength in fall flowerings and 5 to 8 breaks when grown in 10 cm pots for spring flowerings.

B. Foliage:

*Color (upper surface).*—147A.

*Color (under surface).*—147B.

*Shape.*—See photograph.

CHART A

| | KIMBERLY | ADORN |
|---|---|---|
| Ray floret color | Light purple | Purple |
| Capitulum form and type | Flat daisy | Flat daisy |
| Diameter across ace of capitulum | 47 to 52 mm | 75 to 82 mm |
| Branching pattern | Spreading and prolific | Semi-spreading |
| Natural season flower date: | | |
| in Salinas, CA | Sep 2 to 7 | Aug 16 to 22 |
| in Hightstown, NJ | Oct 5 to 17 | Sep 15 to 29 |
| Controlled response | 46 to 53 days | 48 to 53 days |
| Plant height: | | |
| in natural season fall | 30 to 36 cm | 25 to 36 cm |
| in 10 cm pots spring | 18 to 23 cm | 20 to 23 cm |

COMPARISIONS MADE OF PLANTS GROWN UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

I claim:

1. A new and distinct Chrysanthemum plant named Kimberly, as described and illustrated.

* * * * *

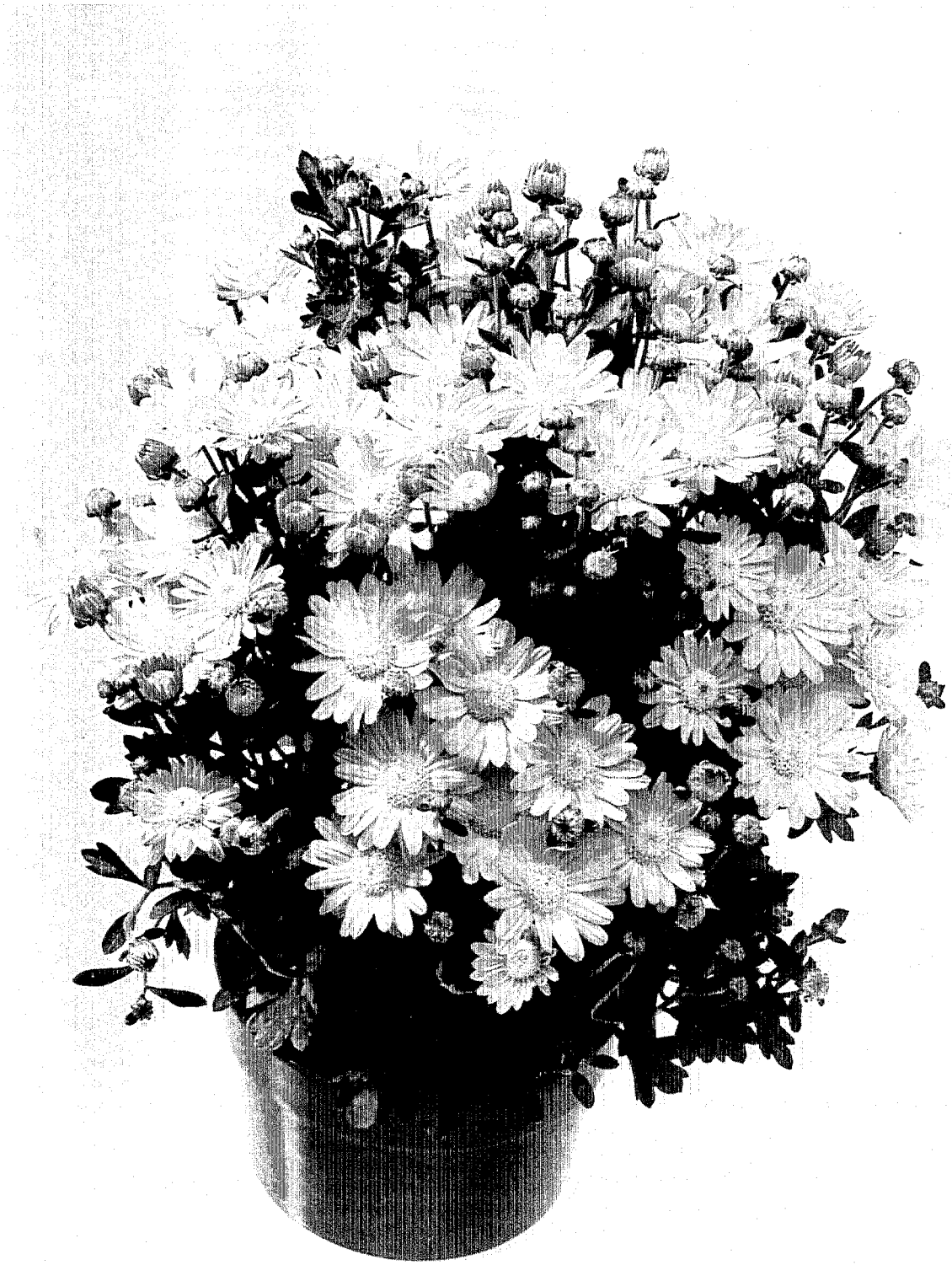

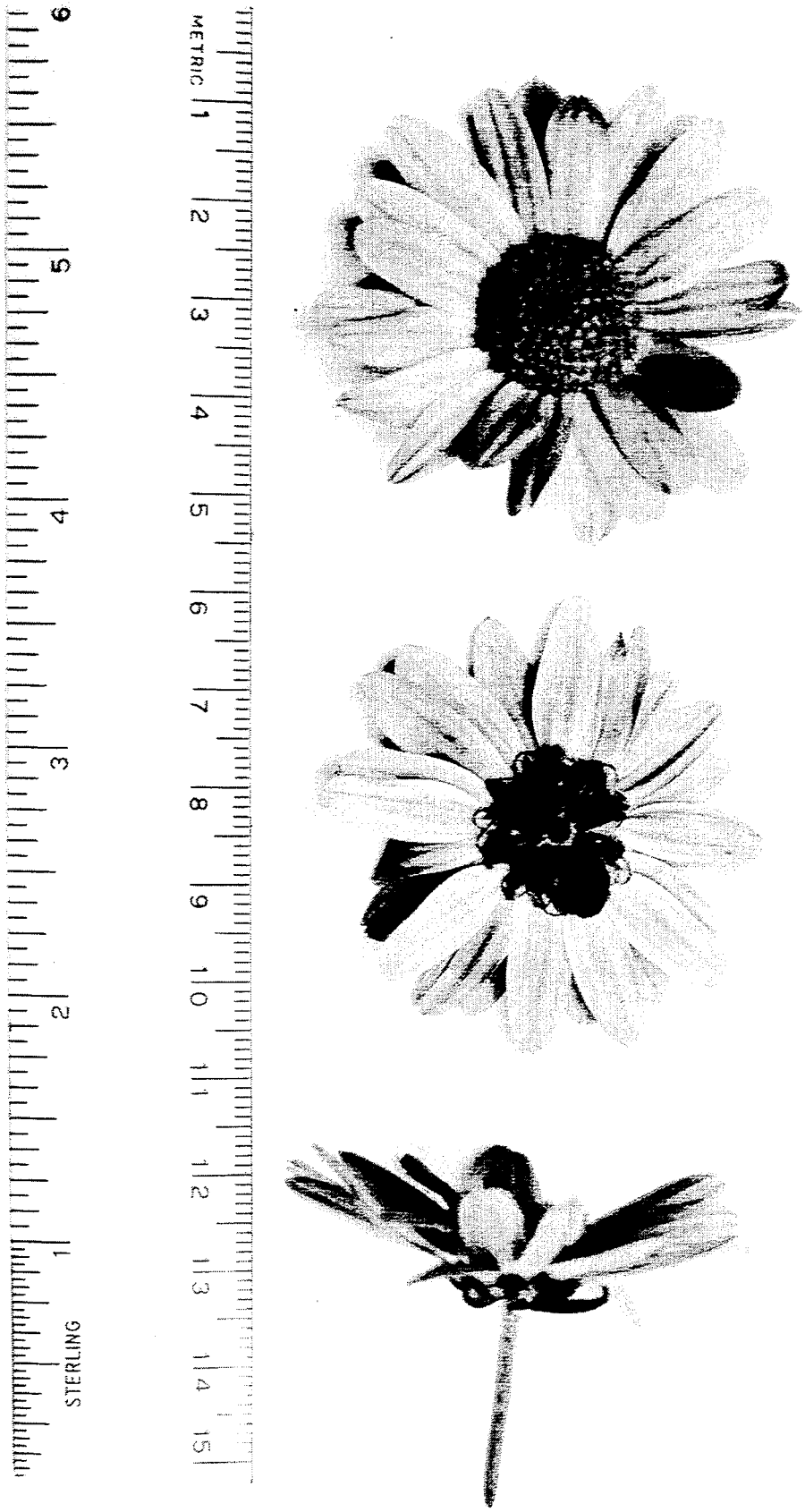
STERLING
METRIC

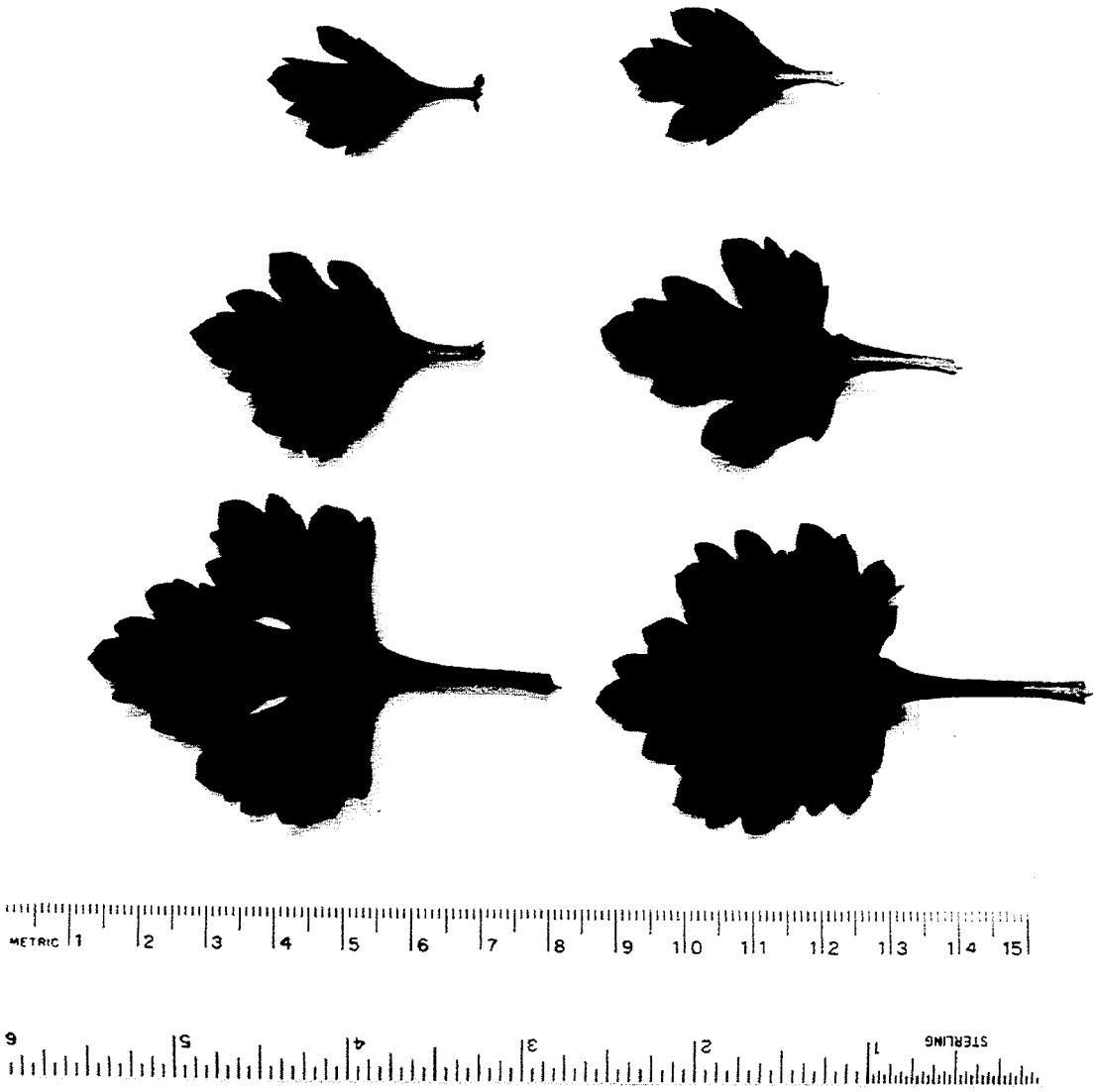
METRIC 1 2 3 4 5 6 7 8 9 10 11 12 13 14 15
STERLING 1 2 3 4 5 6